(12) United States Patent
Bossi et al.

(10) Patent No.: US 9,464,965 B2
(45) Date of Patent: Oct. 11, 2016

(54) METHOD FOR CREATING NON-INSERTED ARTIFICIAL DISBONDS OR DELAMINATIONS FOR NONDESTRUCTIVE INSPECTION TEST STANDARDS

(71) Applicant: The Boeing Company, Chicago, IL (US)

(72) Inventors: Richard H. Bossi, Renton, WA (US); Alan F. Stewart, Renton, WA (US); Marc J. Piehl, Renton, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/536,218

(22) Filed: Nov. 7, 2014

(65) Prior Publication Data

US 2016/0131557 A1 May 12, 2016

(51) Int. Cl.
*G01N 1/00* (2006.01)
*G01N 35/00* (2006.01)
*B29C 59/16* (2006.01)
*B29L 9/00* (2006.01)

(52) U.S. Cl.
CPC .............. *G01N 1/00* (2013.01); *B29C 59/16* (2013.01); *G01N 35/00693* (2013.01); *B29L 2009/00* (2013.01)

(58) Field of Classification Search
USPC ........................ 235/472.03; 156/344, 272.8
See application file for complete search history.

(56) References Cited

U.S. PATENT DOCUMENTS

| 6,848,321 | B2 | 2/2005 | Bossi et al. |
| 7,507,312 | B2 | 3/2009 | Bossi et al. |
| 8,225,664 | B1* | 7/2012 | Sokol .................. G01N 29/041 73/588 |
| 8,785,814 | B1* | 7/2014 | Toller ..................... B23K 26/16 219/121.72 |
| 2005/0067740 | A1* | 3/2005 | Haubensak ........... B08B 7/0042 264/400 |
| 2007/0051469 | A1* | 3/2007 | Bossi ................. B23K 26/0069 156/712 |
| 2008/0075352 | A1* | 3/2008 | Shibuya ............. G01N 21/9501 382/141 |
| 2012/0119336 | A1* | 5/2012 | Akiyama .......... H01L 21/76254 257/629 |
| 2014/0049773 | A1* | 2/2014 | Lahrman ............ G01N 21/8422 356/237.1 |
| 2015/0318210 | A1* | 11/2015 | Budd ...................... H01L 21/78 438/463 |

* cited by examiner

*Primary Examiner* — Allyson Trail
(74) *Attorney, Agent, or Firm* — Felix L. Fischer

(57) ABSTRACT

A method for creation of a non-destructive inspection (NDI) standard employs a coupon of bonded layers or a composite structure having a predetermined thickness. A predetermined pulse width is defined. The coupon and a laser source are positioned with respect to one another and the laser source is used to create a laser pulse having the predetermined pulse width to create a disbond or delamination in the bond layer at a predetermined location. The coupon may then be used as a standard for calibration of NDI inspection tools by scanning the coupon with the tool to provide an inspection output. The output is then examined to confirm that the disbond or delamination in the coupon is properly identified in the output.

19 Claims, 9 Drawing Sheets

METHOD FOR CREATING NON-INSERTED ARTIFICIAL DISBONDS OR DELAMINATIONS FOR NONDESTRUCTIVE INSPECTION TEST STANDARDS

BACKGROUND INFORMATION

1. Field

Embodiments of the disclosure relate generally to composite structure, bonded composite structure and composite structure bonded to metal, and more particularly to inspection standard coupons fabricated from such materials having disbonds or delaminations induced by laser generated stress waves.

2. Background

Non-destructive inspection (NDI) standards are required for the calibration of instrumentation used to inspect structures employing composites, bonded composites and metal bonded to composites. The normal method of creation of the standards is to place inserts in the layup of coupons fabricated from composites or within bond interfaces between composite layers or composite and metal layers during manufacture. While these inserts may correctly represent Foreign Object Debris (FOD), they do not represent true disbonds or delaminations. Accordingly, NDI methods can be sensitive to the insert material or effects due to geometry, and not actually be sensitive to a true disbond or delamination. Thus, the inserts may not be correct representations of the desired defect. At edges of the coupon, it is possible to use an insert during bonding and then extract the insert leaving a gap. However, the resulting gap is not of a naturally occurring size and can only represent an edge delamination.

It is therefore desirable to provide a method for creating standards coupons which have naturally appearing disbond or delamination defects for calibration of NDI instrumentation.

SUMMARY

Exemplary embodiments provide methods for creating non-destructive inspection (NDI) standards employing a coupon having a predetermined thickness. A predetermined pulse width is defined for a laser pulse. The coupon and laser source are positioned with respect to one another and the laser source is used to create the laser pulse having the predetermined pulse width to create the disbond or delamination in the coupon.

The coupon may then be used as a standard for calibration of NDI inspection tools by scanning the coupon with the tool to provide an inspection output. The output is then examined to confirm that the disbond or delamination in the coupon is properly identified in the output.

BRIEF DESCRIPTION OF THE DRAWINGS

The features, functions, and advantages that have been discussed can be achieved independently in various embodiments of the present disclosure or may be combined in yet other embodiments, further details of which can be seen with reference to the following description and drawings.

DETAILED DESCRIPTION

Figure 1A:
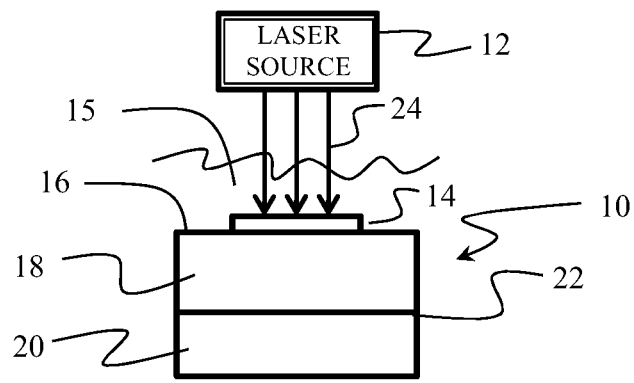
FIG. 1A is a representation of a laminated coupon with two composite layers joined by a bond layer with an ablative layer being impacted by a laser pulse from a laser source.

The methods described herein provide for use of stress waves of sufficient strength to create controlled internal disbonds or delaminations (jointly referred to herein as "defects") in bonded or composite structure, or composite structure bonded to metal, that can then be used as NDI standards. Laser generation of high power stress waves is employed in the embodiments disclosed herein for creating the disbond or delamination.

Referring to the drawings, FIGS. 1A-1D show the structure of an exemplary bonded NDI coupon 10 and sequence of physical effects created by a laser pulse from a laser source 12. An ablative layer 14 is provided on a first surface 16 of the coupon 10 which is a laminate having an first layer 18 and a second layer 20. In an example coupon, the first layer 18 and the second layer 20 are composite sheets. The ablative layer 14 may be an absorbing paint, a PVC tape, or an absorbing fluid. A tamping layer 15, usually water, lies above the ablative layer 14 (more generally, includes a portion that is between the laser source 12 and the ablative layer 14) and acts to reflect the energy of the expanding plasma back into the composite material and enhances the amplitude of the compression wave (discussed below). A bond layer 22 is created by the adhesive bonding the first layer 18 and second layer 20 in a first embodiment of the laminated coupon 10.

Figure 1B:
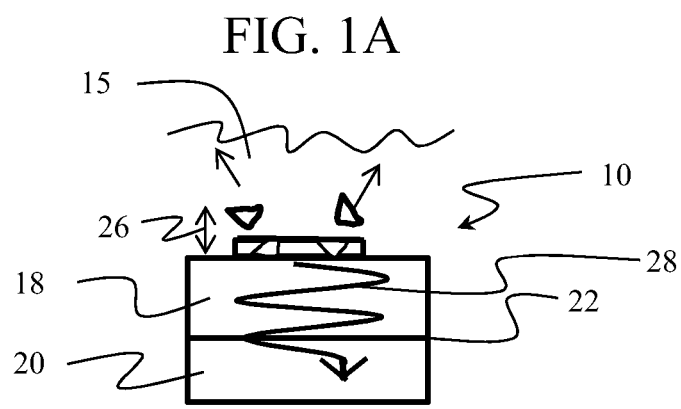
FIG. 1B is a representation of the ablative impact of the laser pulse creating an impulse in the coupon with a compression wave traveling downward from the first surface of the coupon.
Figure 1C:
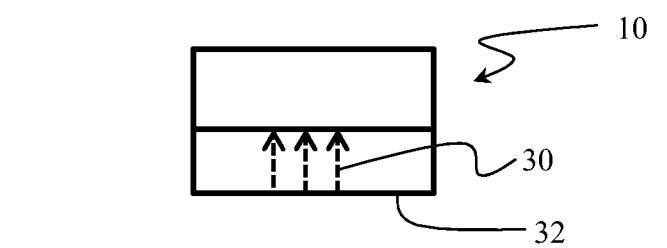
FIG. 1C is a representation of a tension wave reflecting from the opposite surface of the coupon.
Figure 1D:
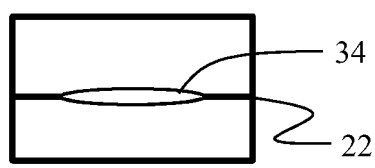
FIG. 1D is a representation of a void created in the bond layer of the coupon by the tension wave in the bond layer.
Figure 1E:
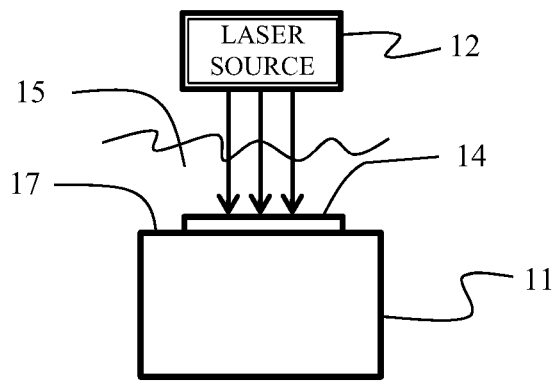
FIG. 1E is a representation of a composite coupon with an ablative layer being impacted by a laser pulse from a laser source.
Figure 1F:
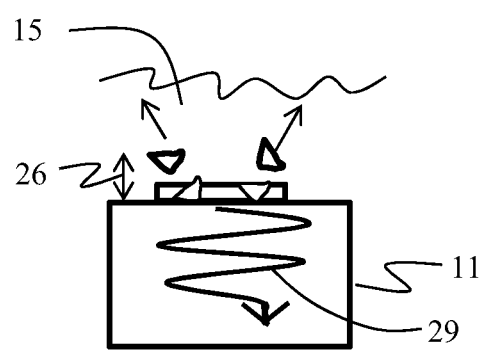
FIG. 1F is a representation of the ablative impact of the laser pulse creating an impulse in the coupon with a compression wave traveling downward from the first surface of the coupon.
Figure 1G:
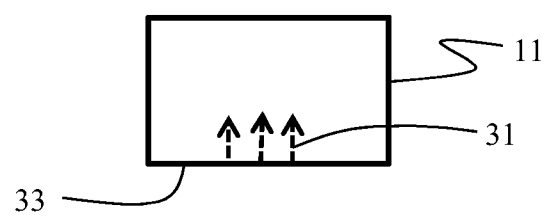
FIG. 1G is a representation of a tension wave reflecting from the opposite surface of the coupon.

The controllable laser source 12 emits a laser pulse (represented by arrows 24 in FIG. 1A) which impacts the ablative layer 14 on a coupon 10 inserted in a target path of the laser source 12. As shown in FIG. 1B, the laser pulse impact and ablation creates an impulse 26 which travels through the coupon 10 as a compression wave represented by sinusoidal wave 28. A reflecting tension wave (represented by arrows 30 as seen in FIG. 1C) is created from the opposing surface 32 of the coupon 10. By control of the laser source 12 to provide a laser pulse 24 to create a desired energy and pulse width in the coupon 10 with a desired beam circumference, as will be described subsequently, the reflecting tension wave 30 propagation will be transmitted to the adhesive bond layer 22 as a weak point, which will break or debond the adhesive layer in an impact area corresponding to the beam circumference or smaller, thereby creating a disbond 34 as the defect in the bond layer 22 as shown in FIG. 1D. In exemplary embodiments, the wavelength of the laser source may be 694.3 nm, 1054 nm, 1064 nm, 1315 nm or any equivalent pulsed laser with sufficient pulse energy. A pulse shape having a 100-300 nsec half width, a spot size ranging from 5 mm to 10 mm in diameter, and a peak fluence (energy/(unit area)) ranging from about 4 $J/cm^2$ to about 100 $J/cm^2$ has been demonstrated to provide the desired disbonds.

Figure 1H:
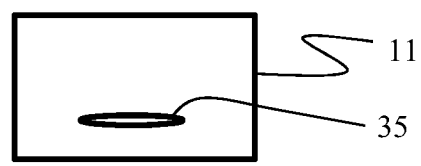
FIG. 1H is a representation of a delamination created in the coupon at the maximum tension point of the tension wave in the coupon.

A composite coupon 11 may be similarly employed to create an NDI standard as shown in FIGS. 1E-1H. As with the bonded coupon, the laser source 12 impacts the ablative layer 14 on a top surface 17 of the coupon 11 (seen in FIG. 1E) and creates an impulse 26 transmitted through the coupon 11 as a compression wave 29 (seen in FIG. 1F). However, upon reflection from the opposing surface 33 (seen in FIG. 1G), the reflecting tension wave 31 creates a peak tension, typically at a point in the coupon where the full tension wave has been reflected as will be described subsequently, and a delamination 35 is created as the defect as shown in FIG. 1H. The depth of the delamination will be dependent on the properties of the composite coupon 11 and the interaction of the tension wave with the composite material. However, the location and diameter of the delamination will be accurately determined by the pulse energy, the diameter of the beam and the location of the beam on the surface of the composite material.

Figure 1I:
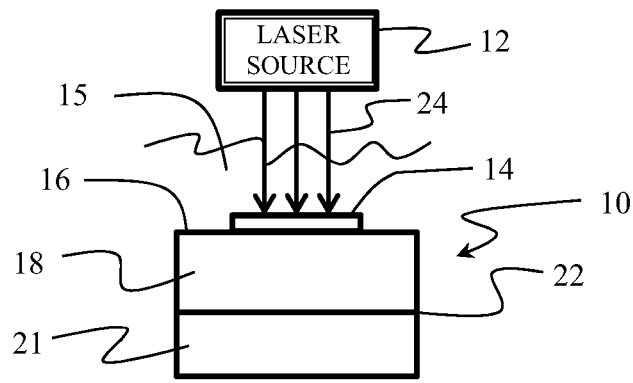
FIG. 1I is a representation of a laminated coupon with a composite layer joined by a bond layer to a metal layer with an ablative layer being impacted by a laser pulse from a laser source.
Figure 1J:
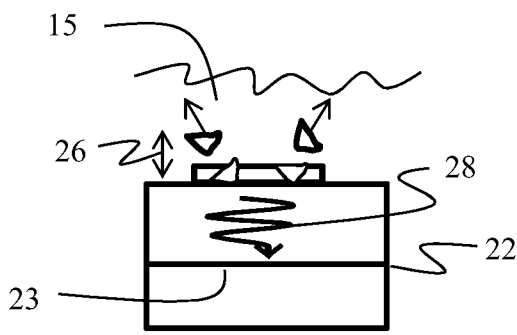
FIG. 1J is a representation of the ablative impact of the laser pulse creating an impulse in the coupon with a compression wave traveling downward from the first surface of the coupon.
Figure 1K:
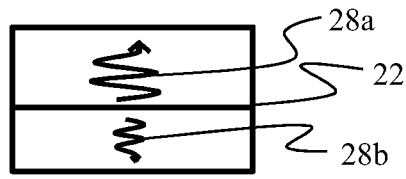
FIG. 1K is a representation of the compression wave being reflected and transmitted from the interface of the bond layer and metal layer.
Figure 1L:
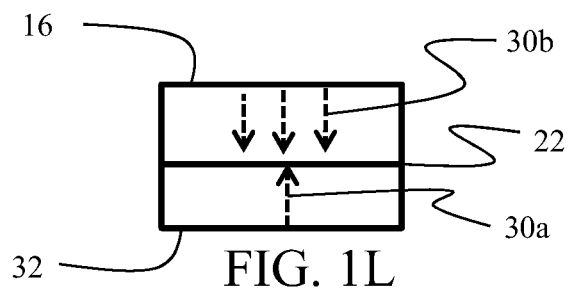
FIG. 1L is a representation of a tension waves reflecting from the top surface of the composite layer and the bottom surface of the metal layer.
Figure 1M:
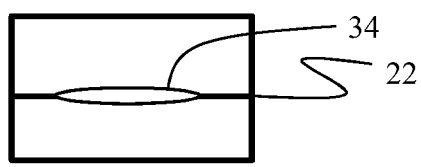
FIG. 1M is a representation of a void created in the bond layer of the coupon by the tension waves in the bond layer.

A coupon created from a composite layer bonded to a metal layer, for example titanium, can also be employed to create an NDI standard as shown in FIGS. 1I-1M. As described previously with respect to the bonded composite layers coupon, the controllable laser source 12 emits a laser pulse 24 as shown in FIG. 1I which impacts the ablative layer 14 on a coupon 10 inserted in a target path of the laser source 12. Coupon 10 has a composite layer 18 and a metal layer 21 with a bond layer 22. As shown in FIG. 1J, the laser pulse impact and ablation (which is enhanced by the action of the tamping layer) creates an impulse 26 which travels through the coupon 10 as a compression wave represented by arrow 28. However, unlike the coupon with two composite layers, the initial compression wave 28 splits at the boundary between the adhesive bond 22 and the metal layer 21. Because the metal layer 21 has a higher acoustic impedance than the composite layer 18, the wave is split into a reflected compression wave 28a and a transmitted compression wave 28b with a lower amplitude as shown in FIG. 1K. A small portion of the compression wave energy is transmitted into the metal (<30% for titanium) which, when it reaches the second surface 32 of the metal layer 21, is reflected back as a first tension wave 30a as shown in FIG. 1L. At substantially the same time, the reflected compression wave 28a in the composite layer 18 reaches the first surface 16 and is reflected back towards the bond layer 22 as a second tension wave 30b. A disbond in the bond layer 22 may then be created based on the reflected tension wave 30b inside the composite layer 18 reaching the bond layer 22, or by the combination of the tension wave 30b in the composite layer and the first tension wave 30a in the metal layer 21 reaching the bond layer 22 as shown in FIG. 1L. The resulting disbond 34 is shown in FIG. 1M. In order for the two tension waves to act cumulatively, the timing of the reflections must be compatible, for example, the thickness of the composite divided by the velocity in the composite layer equal to the thickness of the metal (e.g., titanium) layer divided by the velocity in the metal layer. For titanium and typical carbon-fiber-reinforced polymer (CFRP) composites, that would imply that the thickness of the titanium layer needs to be roughly twice that of the composite layer for both the first and second tension waves 30a, 30b to reach the bond layer 22 at the same time. Otherwise, a disbond at the adhesive layer may be formed solely by the action of the tension wave created by reflection from the first surface of the composite layer.

Figure 2:
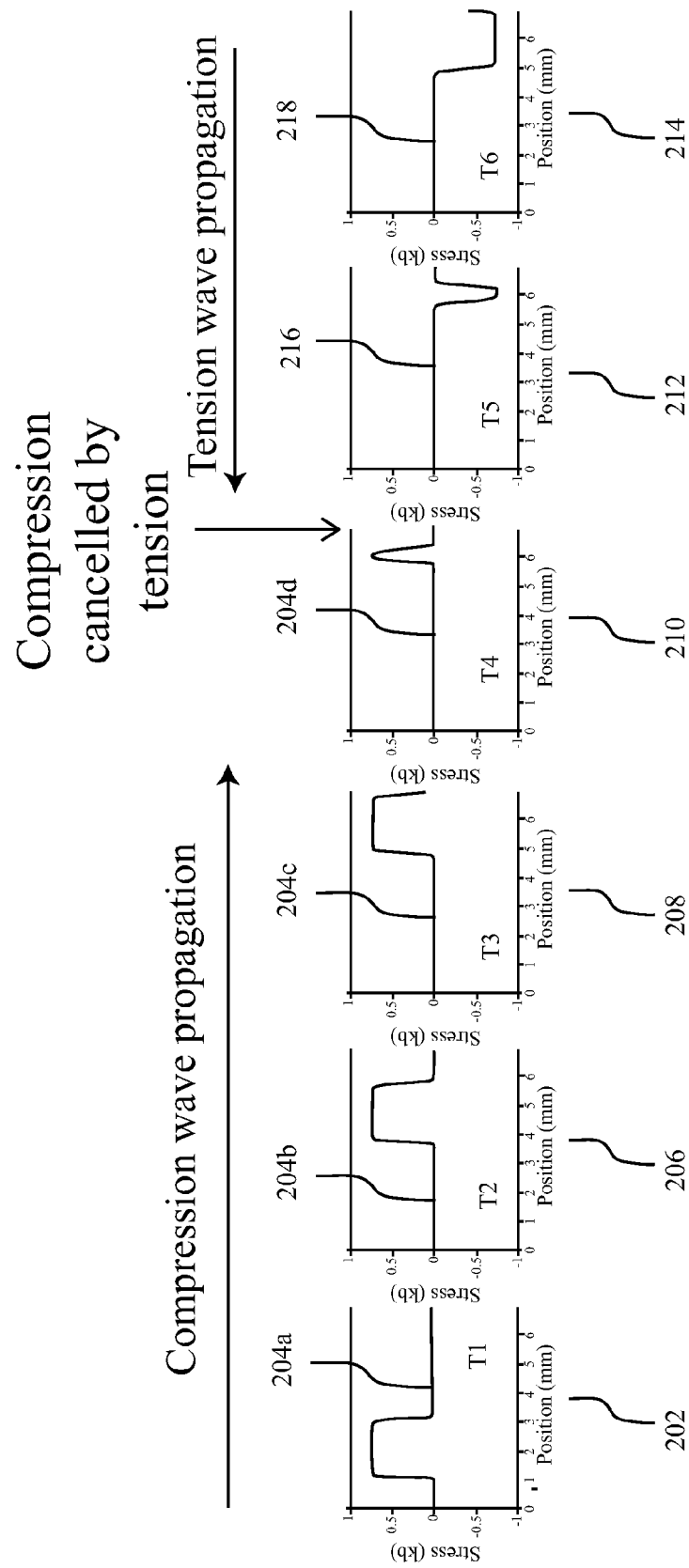
FIG. 2 is a time sequence showing compression wave and tension wave shape and propagation through the coupon.

The physical effect of the propagating compression and tension waves resulting from the laser pulse impact in either of the embodiments described in FIGS. 1A-1D and 1E-1H is shown in FIG. 2. In frame 202 at a first time T1, the compression wave propagating from the first surface 16 has a stress profile 204a shown relative to the position (depth) within the coupon shown in millimeters. The stress profile 204b is shown at T2 in frame 206 and profile 204c is shown in frame 208 at time T3 both with essentially the same shape as profile 204a. However, at time T4 shown in frame 210, the stress profile 204d has been altered due to cancellation by the reflecting tension wave propagating from the opposing surface. Frames 212 and 214 show the stress profile 216 of the emerging tension wave at time T5 and the reflecting stress profile 218 at time T6. For the bonded coupon 10 as described with respect to FIGS. 1A-1D, the tension wave will typically result in a disbond in the bond line when the tension wave passes through the bond line as described. For the composite coupon as described with respect to FIGS. 1E-1H, the location of the delamination is determined by the strength of the composite coupon and where the tension wave has the greatest amplitude. If the coupon has uniform strength throughout, the delamination will most likely appear at the location where the tension wave is fully formed after reflection from the opposing surface. Otherwise, the delamination will form at the weakest location within the coupon.

Figure 3:
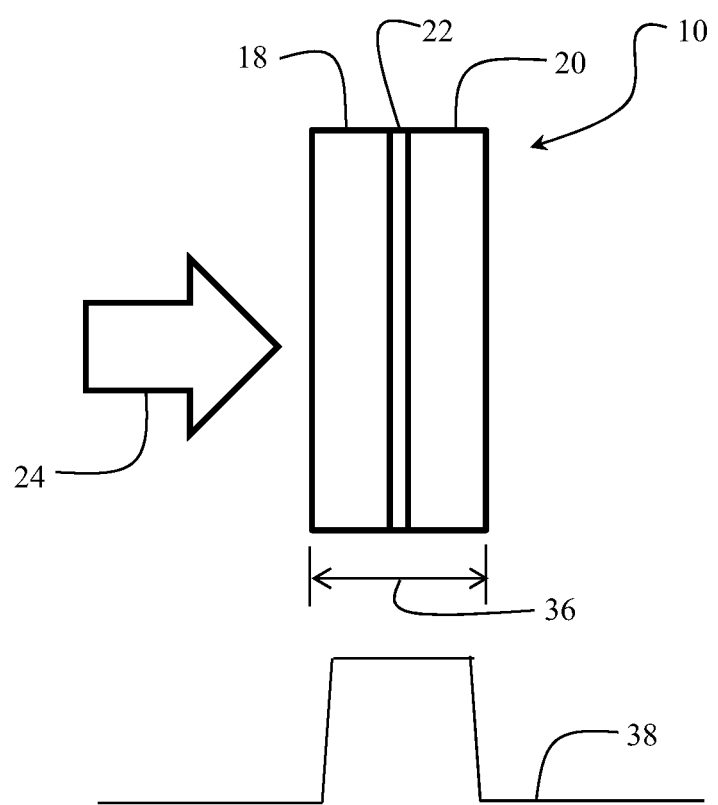
FIG. 3 is a representation of the coupon layers showing a laser generated compression pulse width less than the thickness of the bonded structure.

FIG. 3 shows an example of a coupon 10 having an adhesive bond layer 22. The compression pulse width, represented by trace 38 (from impulse received from laser pulse 24), is desirably shorter than its travel time through the structure having total thickness 36 (the sum of thicknesses of the first layer 18, bond layer 22 and the second layer 20 or the total coupon thickness for a composite coupon 11 as previously described with respect to FIGS. 1I-1M). In exemplary applications for coupons representing primary structural components, a pulse width of ¼ to ⅓ the total coupon thickness 36 has been demonstrated to provide efficacious results. Location of peak tension in the coupon 10 is determined by pulse duration and the acoustic properties of the composite material, as well as attenuation of the waves due to propagation distance in the composite material.

Figure 4:
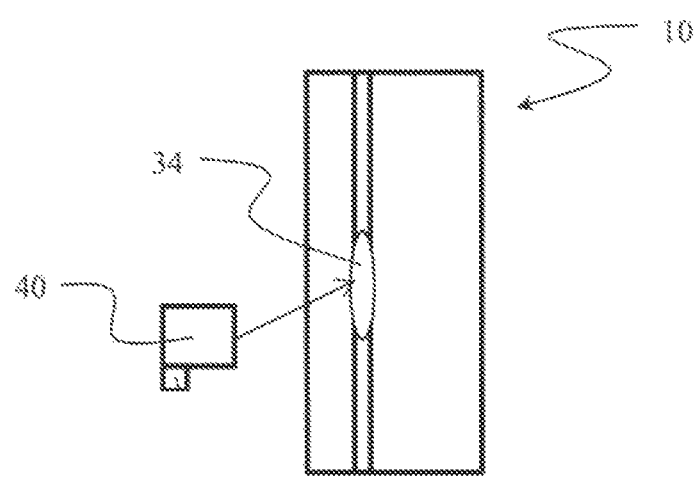
FIG. 4 is a side section view of a coupon with the induced disbond in the bond layer to be used as a standard for NDI tools.

As shown in FIG. 4, the coupon 10 (or coupon 11) may then be employed as an NDI standard for calibration or confirmation of an NDI inspection tool 40 which may include such devices as ultrasonic scanners (including phased array devices), computerized tomography (CT) scans, vibration analyzers, shearography tools and thermography inspection devices. The inspection tool 40 is operated in the normal manner with respect to coupon 10 (or coupon 11) to attempt to identify and characterize disbond 34 (or delamination 35) as a defect.

Figure 5:
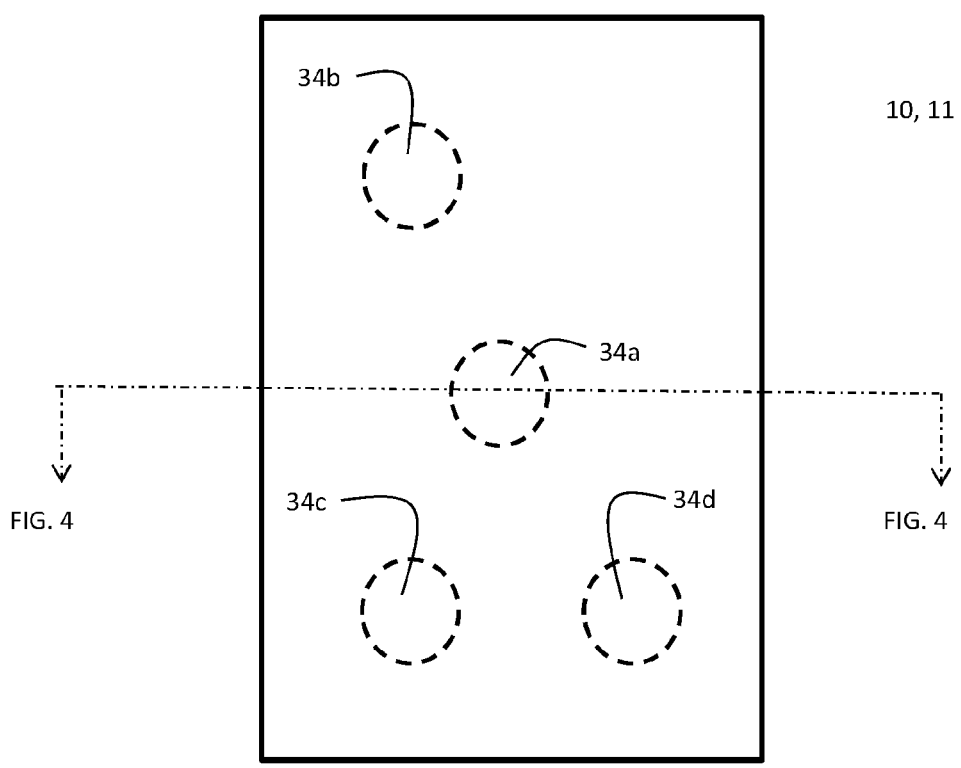
FIG. 5 is a top view of the coupon with multiple disbonds created by sequentially pulsing the laser source along a predetermined path over the coupon; and, FIGS. 6A and 6B are a flowchart of a method for implementing the disclosed embodiments.

Control of the laser pulse in creation of the coupon for pulse width, beam shape, impulse power and impact location provides specifically known defect size and location. As shown in FIG. 5, multiple defects (exemplified as 34a, 34b, 34c and 34d) may be introduced into the coupon for purposes of use as an NDI standard. Sequential pulsing of the laser while traversing the laser along a specified path may be employed to create a shaped defect or defect profile in the adhesive layer. Both forms of defects may be employed for confirmation of the ability of the inspection tool 40 to observe and properly characterize the defect(s). In most instances, once the laser source is calibrated for the coupon materials and dimensions, the size, shape and location of the defects may be pre-determined based on pulse width, beam shape, impulse power and impact location. Then, the defects may be created using such parameters. Alternatively, matching coupons may be created, such that one of the matching coupons is dissected for confirmation of defect size, location and shape. Inspection of the created NDI standard using a precalibrated metrology NDI tool may be accomplished as yet another alternative.

Figure 6A:
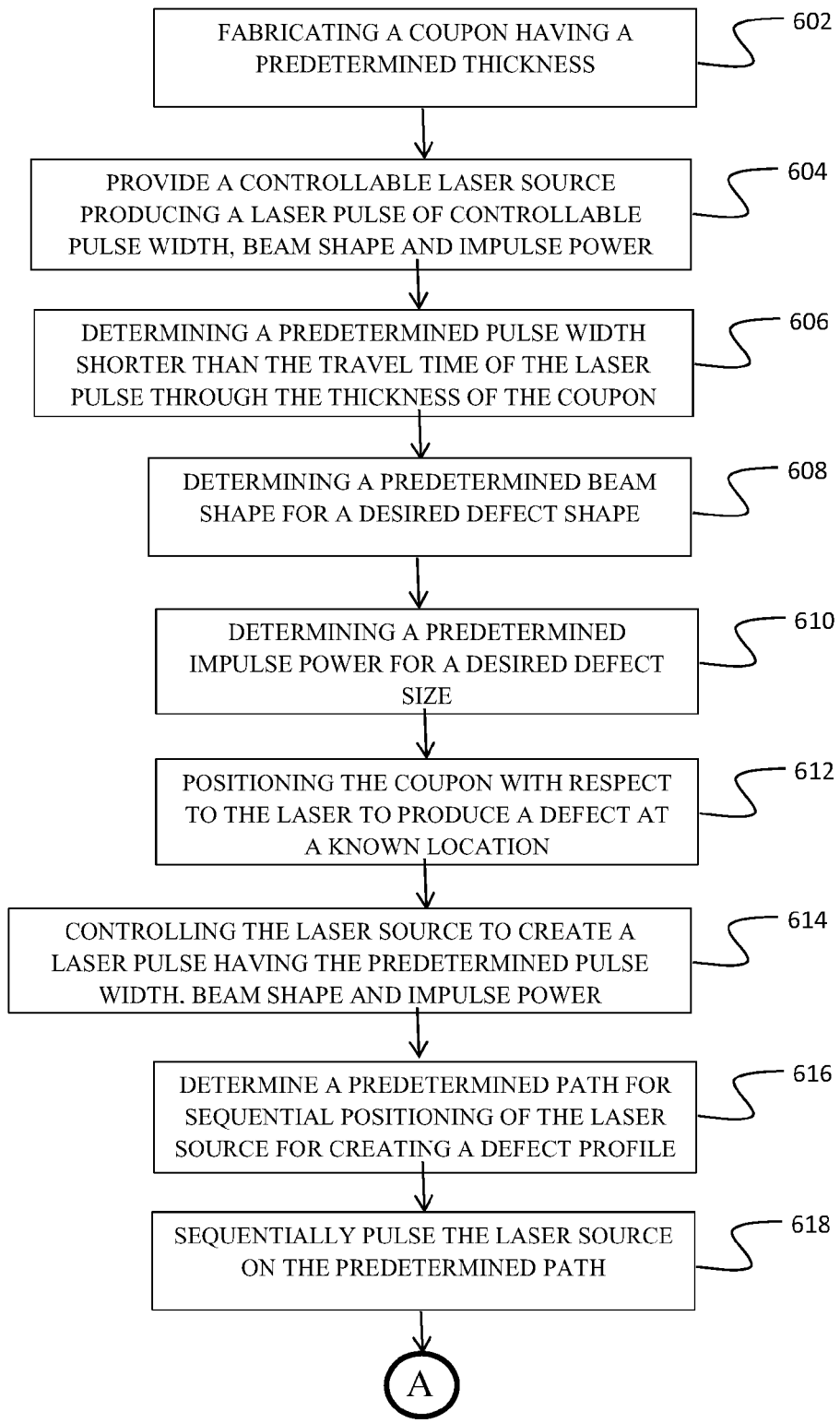
Figure 6B:
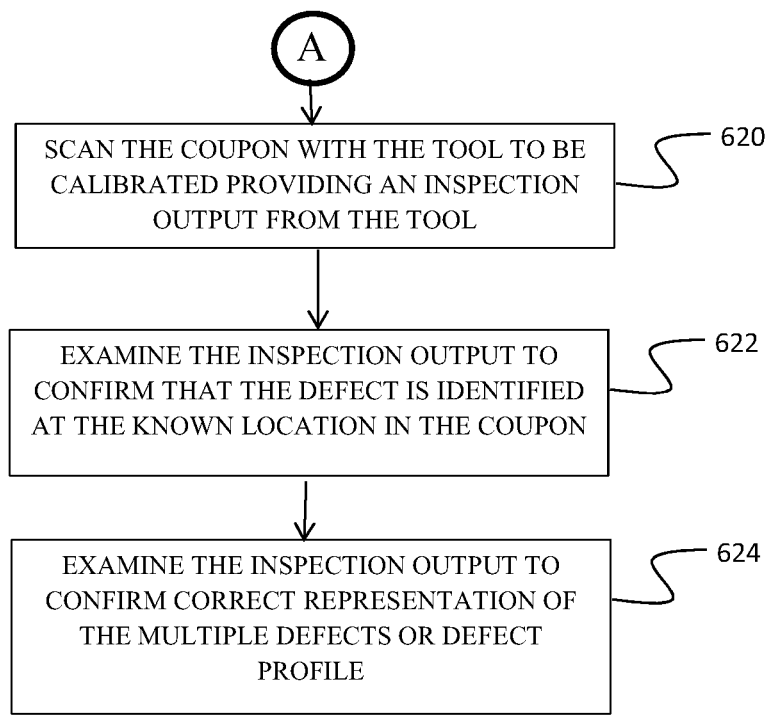

As shown in FIGS. 6A and 6B, a method for creation of a non-destructive inspection (NDI) standard using the embodiments described includes fabricating a coupon having a predetermined thickness, which may have a first layer of composite, at least one adhesive bond layer and at least one second layer of composite, may be a composite structure, or may be a laminate with a first composite layer, a bond layer and a metal layer, step 602. A controllable laser source capable of producing a laser pulse with a controllable pulse width, beam shape and impulse power is provided, step 604. Determinations are made for a predetermined pulse width shorter than the travel time of the laser pulse through the thickness of the coupon, step 606, a predetermined beam shape for a desired defect shape, step 608, and a predetermined impulse power for a desired defect size, step 610. The coupon and laser source are then positioned with respect to each other to produce a defect at a known location in the coupon, step 612, and the laser source is controlled to create the laser pulse having the predetermined pulse width, the predetermined beam shape and predetermined impulse power to create at least one defect in the coupon, step 614. Additionally, a predetermined path may be established for sequential positioning of the laser source with respect to the coupon or the coupon with respect to the laser source for creating a defect profile, step 616. The laser source may then be sequentially pulsed on the predetermined path to create the defect profile, step 618.

The standard coupon may then be used to calibrate NDI inspection tools by scanning the coupon with the tool to be calibrated, step 620, and providing an inspection output from the tool. The inspection output is then examined to confirm that the defect is identified at the known location in the coupon, step 622, with the predetermined shape and size. If a defect profile or multiple defect locations have been created by sequentially moving the laser source along the predetermined path, the inspection output in then examined to confirm correct representation of the multiple defects or defect profile, step 624.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

What is claimed is:

1. A method for creating a non-destructive inspection (NDI) standard, the method comprising:
   selecting a coupon which is a laminate, said coupon having a predetermined thickness;
   defining a predetermined pulse width;
   positioning the coupon and a laser source relative to one another; and,
   using the laser source to generate a laser pulse having the predetermined pulse width to impact a first surface of the coupon creating an impulse which travels through the coupon as a compression wave with a reflecting tension wave created from an opposing surface of the coupon, the reflecting tension wave propagation transmitted to a laminate layer as a weak point, resulting in a delamination or disbond at the laminate layer in an impact area to create at least one defect in the coupon, wherein the predetermined pulse width is shorter than a travel time of the laser pulse through the thickness of the coupon.

2. The method as defined in claim 1 wherein the laser source is controllable to produce a laser pulse with a controllable pulse width, beam shape and impulse power.

3. The method as defined in claim 1 wherein the laser pulse has a beam shape and wherein the beam shape produces a desired defect shape.

4. The method as defined in claim 3 wherein the laser pulse has an impulse power and wherein the impulse power produces a desired defect size.

5. The method as defined in claim 1 further comprising:
   defining a predetermined path for sequentially positioning the laser source and the coupon relative to one another for creating a defect profile; and,
   sequentially pulsing the laser source on the predetermined path to create the defect profile.

6. The method as defined in claim 1 wherein the coupon is a bonded coupon having a first layer and a second layer with an intermediate adhesive bond, and the step of using the laser source creates a disbond in the adhesive bond as the defect.

7. The method as defined in claim 1 wherein the coupon is a composite coupon and the step of using the laser source creates a delamination in the composite as the defect.

8. A method for calibrating a non-destructive inspection (NDI) tool comprising:
   preparing a standard by
   selecting a coupon which is a laminate having a predetermined thickness;
   defining a predetermined pulse width;
   positioning the coupon with respect to a laser;
   controlling a laser source to create a laser pulse having the predetermined pulse width to impact a first surface of the coupon creating an impulse which travels through the coupon as a compression wave with a reflecting tension wave created from an opposing surface of the coupon, the reflecting tension wave propagation transmitted to a laminate layer as a weak point, resulting in a delamination or disbond at the laminate layer in an impact area to create at least one defect in the coupon at a known location;

using the standard that includes the at least one laser-produced defect therein, wherein the defect is in a known location;

scanning the standard with an NDI tool to produce an inspection output; and, examining the inspection output to confirm that the at least one defect is identified at the known location in the standard.

9. The method as defined in claim 8 wherein the controllable laser source produces the laser pulse with a controllable pulse width, beam shape and impulse power.

10. The method as defined in claim 8 wherein the predetermined pulse width is shorter than a travel time of the laser pulse through the thickness of the coupon.

11. The method as defined in claim 10 wherein the step of preparing the standard further comprises:

defining a predetermined beam shape for a desired defect shape; and, the step of controlling the laser source further comprises creating the laser pulse having the predetermined beam shape; and, the step of examining the inspection output includes confirming the defect shape.

12. The method as defined in claim 11 wherein the step of preparing the standard further comprises:

defining a predetermined impulse power for a desired defect size; and, the step of control the laser source further comprises creating the laser pulse having the predetermined impulse power; and, the step of examining the inspection output includes confirming the defect size.

13. The method as defined in claim 12 wherein the step of preparing the standard further comprises:

defining a predetermined path for sequential positioning of the laser source with respect to the coupon for creating a defect profile; and, the step of controlling the laser source further comprises sequentially pulsing the laser source on the predetermined path to create the defect profile; and, the step of examining the inspection output includes confirming the defect profile.

14. An apparatus for creating a non-destructive inspection (NDI) standard comprising:

a coupon having a predetermined thickness;

a laser source capable of producing a laser pulse having a predetermined pulse width;

said coupon and the laser positioned with respect to one another to produce a defect at a known location in the coupon; and, said laser source used to create the laser pulse having the predetermined pulse width to impact a first surface of the coupon creating an impulse which travels through the coupon as a compression wave with a reflecting tension wave created from an opposing surface of the coupon, the reflecting tension wave propagation transmitted to a laminate layer as a weak point, resulting in a delamination or disbond at the laminate layer in an impact area to create the at least one defect.

15. The apparatus as defined in claim 14 wherein the laser source produces a laser pulse with a controllable pulse width, beam shape and impulse power.

16. The apparatus as defined in claim 14 wherein the predetermined pulse width is shorter than a travel time of the laser pulse through the thickness of the coupon.

17. The apparatus as defined in claim 16 wherein:

a predetermined beam shape for the laser pulse is defined for a desired defect shape; and, the laser source is controlled to create the laser pulse having the predetermined beam shape.

18. The apparatus as defined in claim 17 wherein:

a predetermined impulse power for the laser pulse is defined for a desired defect size; and, said laser source further is controlled to create the laser pulse having the predetermined impulse power.

19. The apparatus as defined in claim 18 wherein:

the laser source is sequentially positionable along a predetermined path with respect to the coupon for creating a defect profile; and, said laser source is sequentially pulsed on the predetermined path to create the defect profile.

* * * * *